United States Patent [19]

Shapland et al.

[11] Patent Number: 4,817,608
[45] Date of Patent: Apr. 4, 1989

[54] CARDIOVERTING TRANSVENOUS CATHETER/PATCH ELECTRODE SYSTEM AND METHOD FOR ITS USE

[75] Inventors: J. Edward Shapland; Stanley M. Bach, Jr., both of Shoreview, Minn.

[73] Assignee: Mieczyslaw Mirowski, Owings Mills, Md.

[21] Appl. No.: 56,044

[22] Filed: May 29, 1987

[51] Int. Cl.$^4$ ............................................. A61N 1/00
[52] U.S. Cl. ................................................ 128/419 P
[58] Field of Search .................. 128/419 PG, 419 D

[56] References Cited

U.S. PATENT DOCUMENTS

| Re. 27,757 | 9/1973 | Mirowski | 128/419 D |
|---|---|---|---|
| 3,942,536 | 3/1976 | Mirowski et al. | 128/419 D |
| 4,030,509 | 6/1977 | Heilman et al. | 128/419 D |
| 4,161,952 | 7/1979 | Kinney et al. | 128/786 |
| 4,270,549 | 6/1981 | Heilman | 128/419 D |
| 4,407,288 | 10/1983 | Langer et al. | 128/419 D |
| 4,548,203 | 10/1985 | Tacker, Jr. et al. | 128/419 D |
| 4,603,705 | 8/1986 | Speicher et al. | 128/786 |
| 4,662,377 | 5/1987 | Heilman et al. | 128/419 P |
| 4,708,145 | 11/1987 | Tacker, Jr. et al. | 128/41 PD |

Primary Examiner—Francis J. Jaworski
Assistant Examiner—George Manuel
Attorney, Agent, or Firm—Fleit, Jacobson, Cohn & Price

[57] ABSTRACT

Disclosed are an electrode configuration and a method for its use with an automatic implantable cardioverter/defibrillator. The electrode configuration includes a catheter electrode intravenously positioned within the heart of a patient wherein one electrode, defined by the catheter, is within the right ventricle and a second electrode, also defined by the catheter and spaced from the first electrode, is within the superior vena cava region. A third electrode, in the form of a flexible, substantially planar patch, is subcutaneously positioned outside the thoracic cavity in the region of the left ventricle. At the time of electrical discharge, or permanently, the first and second electrodes of the catheter are connected together. The electrode arrangement can be implanted without opening of the thoracic cavity by intravenously placing the catheter electrode within the heart of a patient and subcutaneously implanting the patch electrode between the skin and the thoracic cavity. The automatic implantable cardioverter/defibrillator senses life-threatening arrhythmic conditions of the heart and issues at least one cardioverting or defibrillating pulse that is applied between the electrode positioned in the region of the left ventricle and the commonly connected catheter electrodes positioned, respectively, in the right ventricle and within the superior vena cava region. The catheter also includes a pacing tip.

18 Claims, 1 Drawing Sheet

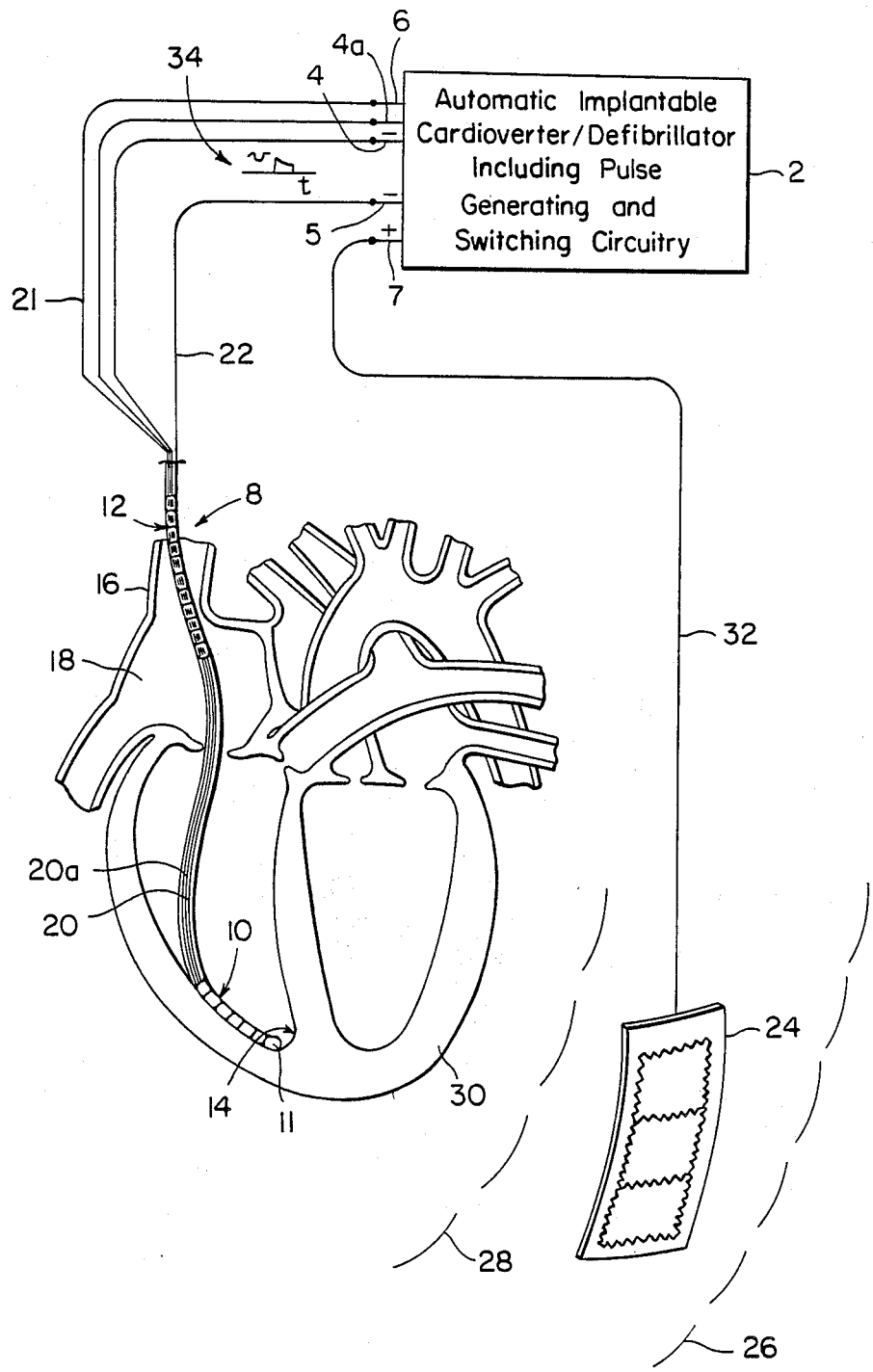

CARDIOVERTING TRANSVENOUS CATHETER/PATCH ELECTRODE SYSTEM AND METHOD FOR ITS USE

BACKGROUND OF THE INVENTION

The present invention relates to a novel electrode arrangement and method for effecting cardioversion with an automatic implantable device. The electrode arrangement includes a catheter electrode intravenously positioned within the heart of a patient wherein one electrode on the catheter is within the left ventricle and a second electrode on the catheter is within the superior vena cava or in the right atrium. A third electrode, in the form of a flexible, substantially planar patch, is subcutaneously positioned outside the thoracic cavity in the region of the left ventricle. The two electrodes on the catheter are electrically connected together during a discharge, and are placed at a polarity opposite from that of the patch electrode.

Approximately 250,000 Americans under the age of 65 die annually from a condition termed "sudden cardiac death". In the vast majority of these cases, the cause of death is ventricular tachycardia and/or ventricular fibrillation. An automatic implantable cardioverting/defibrillating device has been developed and shown to be effective in preventing sudden cardiac death from these causes. See, for example, U.S. Pat. No. 4,407,288.

As used herein, the term cardioversion generally may be defined as the correction of either ventricular tachycardia or ventricular fibrillation by the discharge of electrical energy into the heart (0.1–40 joules when discharged through internal electrodes). Ventricular tachycardia is an abnormally rapid heart rate (120–180 beats per minute) originating in the heart's main pumping chambers (ventricles) which is regular in periodicity and oftentimes is life threatening to the patient. Ventricular fibrillation is generally a more rapid heartbeat disorder, disorganized and irregular, or non-periodic, and is fatal unless corrected within minutes by the discharge of electrical energy through the heart. More specific medical terminology often uses the term cardioversion to mean the synchronized delivery of an electrical shock to the heart to correct ventricular tachycardia. Defibrillation, then, is often referred to as the nonsynchronized delivery of electrical energy to the heart to correct ventricular fibrillation. Internal cardioversion is usually effective with. 0.1 to 3 joules of electrical energy when delivered in synchronism with the electrical heartbeat. Internal defibrillation requires 5 to 30 or more joules of electrical energy, depending largely on the electrode system used.

Over the years, many different types of electrode systems have been suggested for use with the automatic implantable cardioverter/defibrillator. For example, U.S. reissue Pat. No. Re. 27,757 describes an electrode arrangement whereby one electrode is formed on the distal end of an intravascular catheter that is positioned within the right ventricle, whereas the second electrode is positioned on the surface of the chest or sutured under the skin of the chest wall or directly to the ventricular myocardium.

U.S. Pat. No. 3,942,536 discloses a catheter electrode system wherein both electrodes are on a single intravascular catheter. The distal electrode is wedged in the apex of the right ventricle and the proximal electrode is immediately superior to the right atrium.

An improved intravascular catheter electrode system is described in U.S. Pat. No. 4,603,705. There, the proximal electrode is located in the superior vena cava and the distal electrode is in the right ventricle. A sensing and pacing electrode is also provided at the distal tip of the catheter. The first two electrodes constitute the anode and cathode of the cardioverting/defibrillating electrode pair; the tip electrode is used for sensing heart rate and pacing the heart. Using this single catheter system, energies required to defibrillate the human heart have been found to vary between 5–40 joules, but in some 40–50% of patients, even the higher energies may be insufficient to defibrillate the heart. Thus, although this improved catheter electrode system has many advantages, such as the capability of being installed without surgically invading the thoracic cavity, it has been found to have somewhat limited effectiveness in terminating ventricular anhythmias.

Various other electrode arrangements have also been employed. In U.S. Pat. No. 4,030,509, for example, the implantable electrode system includes, among others, a flexible apex electrode designed to surround the apex of the heart, and various flexible base electrodes designed to surround the base of the heart.

Another electrode arrangement and discharge method can be found in U.S. Pat. No. 4,548,203. There, three or more patch electrodes are connected and used in a discharge pattern involving the sequential delivery of multiple shocks across the heart, with such sequential shocks being in transverse directions to one another. The patentees explain that by issuing sequential shocks across opposed pairs of electrodes, a more uniform discharge pattern develops, resulting in more effective cardioversion and hence lower discharge energies.

Typical electrodes presently being used in conjunction with the commercially available automatic implantable cardioverter/defibrillator consist of one catheter defibrillating electrode adapted to be placed in the superior vena cava/right atrial region, and a second flexible, conformal, defibrillating patch electrode adapted to be placed on the outside of the heart, typically over the lateral wall of the left ventricle. See, U.S. Pat. Nos. 4,161,952 and 4,270,549. Placement of the first catheter-mounted electrode can be accomplished by insertion into one of the veins outside the thorax and sliding the catheter electrode into the venous system until the electrode portion is within the thorax and located at the junction of the superior vena cava and right atrium. Thus, for the placement of this electrode, it is not necessary to surgically enter the thorax. For the second electrode, however, it is necessary to make one of a variety of surgical incisions to open the thoracic cavity in order to place the electrode over the left ventricle of the heart. Each of these surgical approaches has disadvantages. Two such approaches involve major surgery and substantial patient recovery time with a cost currently between $8,000–12,000. These approaches consist of splitting the sternum (breastbone) or alternatively opening a space between the ribs in order to gain access to the surface of the heart. A third approach involves making a smaller incision under the xiphoid process, which is simpler from a surgical point of view, but still involves entering the thoracic cavity. Moreover, this approach sometimes does not allow convenient positioning of the left ventricular electrode. And in many instances, two patch electrodes are used, rather than one patch and one catheter electrode.

With this background, there was developed an electrode arrangement and discharge method which does not involve the surgical opening of the thoracic cavity. Specifically, in copending U.S. patent application Ser. No. 795,781, filed on Nov. 7, 1985 and assigned to the present assignee, incorporated herein by reference, there is disclosed an electrode system that includes an intravascular catheter insertable within the heart of a patient, and having a first electrode adjacent the distal end of the catheter and a second electrode positioned at the proximal end of the catheter; this catheter electrode can be of the type described in Pat. No. 4,603,705, incorporated herein by reference. Associated with this bipolar catheter electrode is a third electrode, in the form of a flexible patch electrode, that is placed subcutaneously outside the thoracic cavity, but proximate the apex of the left ventricle. The patch electrode is electrically connected with the second electrode of the catheter, the latter of which is positioned in the superior vena cava/right atrium region. The first, or distal, electrode of the catheter, completes the cardioverting/defibrillating circuit. A pulse of electrical energy is discharged between the first electrode and the combined second electrode/patch electrode.

It subsequently has been theorized that while the electrode placements and connections as described immediately above does, indeed, reduce the energy needed for effective cardioversion/defibrillation, it may be possible to still further reduce the necessary discharge energy. Specifically, by changing the polarity of discharge so that the discharge travels more effectively and uniformly across the myocardium, it may be possible to effect cardioversion at even lower energies with a single shock.

SUMMARY OF THE INVENTION

The present invention relates to a transvenous catheter and patch electrode arrangement that is implantable without the need to enter the thoracic cavity and that is believed to effectively result in a discharge that is uniform across a major portion of the myocardium so that cardioversion/defibrillation can be effected at reduced energy levels. Specifically, it is contemplated that a bipolar catheter electrode be placed intravascularly so that one of its two electrodes resides deep in the right ventricle and the other of its electrodes resides in the superior vena cava or in the right atrium. A third electrode, in the form of a patch, can be positioned subcantaneously so as to reside in the region of the left ventricle. An implantable cardioverter/ defibrillator of the type now well-known is associated with the three above-described electrodes, and delivers cardioverting pulses to the heart through the electrodes in such manner that the two poles of the catheter electrode are electrically connected in common, and act against the patch electrode that is held at the opposite polarity.

By having the two catheter electrodes at the same potential, the discharge acting against the patch is believed to be spread over a larger volume of the myocardium, yet without any shunting between the relatively closely spaced catheter electrodes by the resident blood. In this regard, it should be noted that the resistivity of blood is lower than that of myocardial tissue. Although this effect is more pronounced at lower currents, it still is significant with the high-current discharges involved in cardioversion through implanted electrodes. Therefore, with the present electrode arrangement, the effectiveness of the electrical discharge is enhanced. In dogs, with identical electrodes and electrode placements, it has been found that the connection described in copending application Ser. No. 795,781, now U.S. Pat. No. 4,708,145 required on the order of 23 joules for effective cardioversion in 80% of the episodes, while the connection of the present invention required only on the order of 16 joules for the same 80% effective cardioversion. Such decrease in energy level is extremely important, especially for an implantable device, because it could result in longer implant life and/or smaller implant size, and also could result in less trauma to cardiac tissue and less discomfort to the patient if conscious when a discharge is delivered.

It thus is an object of the present invention to provide a new and improved electrode arrangement for an automatic implantable cardioverter/defibrillator that does not require the surgical opening of the thoracic cavity.

A further object of the present invention is to provide a new and improved electrode system that requires lesser energy levels to effectively cardiovert or defibrillate an ailing heart.

Further, it is an object of the present invention to provide a minimally invasive automatic implantable cardioverter/defibrillator system that passe the majority of its current through the left ventricle upon discharging. This is accomplished by means of an implantable electrode arrangement including an intravascular catheter electrode having a first electrode adjacent the distal end of the catheter for positioning in the right ventricle and a second electrode, spaced from the first electrode, for positioning in the superior vena cava region. This catheter electrode is used in conjunction with a subcutaneous patch electrode, positioned outside the thoracic cavity in the region of the left ventricle. The two electrodes on the catheter are electrically connected together, and are discharged against the patch electrode. Thus, the first and second electrodes of the catheter are connected at one polarity to an implantable pulse generator, whereas the patch electrode is connected at the opposite polarity to the pulse generator.

It is also an object of the present invention to provide a method for automatically cardioverting/defibrillating the heart of a patient by detecting an arrhythmic condition and automatically applying a voltage pulse of a magnitude sufficient to restore normal cardiac rhythm, the pulse being applied between, on the one hand, a first and a second electrode located within the right ventricle of the heart and in the superior vena cava region, respectively, and, on the other hand, a third electrode positioned in the region of the left ventricle outside the thoracic cavity.

Still further, it is an object of the present invention to provide a method of implanting and utilizing electrodes in an automatic implantable cardioverter/defibrillator system without surgically opening the thoracic cavity. The method includes the steps of intravenously inserting a catheter having first and second electrodes such that the first electrode is within the right ventricle and the second is in the superior vena cava region, subcutaneously placing a patch electrode outside the thoracic cavity, and electrically connecting the two catheter electrodes together during discharge.

These and other objects of the present invention will be apparent when reference is made to the following detailed description and drawing.

BRIEF DESCRIPTION OF THE DRAWING

The sole FIGURE of the drawing illustrates the novel electrode arrangement of the present invention in conjunction with an automatic implantable cardioverter/defibrillator system.

DETAILED DESCRIPTION OF A PREFERRED EMBODIMENT

With reference to the sole FIGURE of the drawing, an automatic implantable cardioverter/defibrillator 2, such as the type described in U.S. Pat. No. 4,407,298, is implanted within the abdominal region of the patient and is coupled with electrodes associated with the heart of the patient. The automatic implantable cardioverter/defibrillator 2 includes sensing and detecting circuitry, as well as pulse generating circuitry, coupled to the implantable electrodes. The cardioverter/defibrillator 2 senses an arrhythmic condition of the heart and, in response thereto, issues or emits cardioverting or defibrillating pulses to the heart, through the implantable electrodes. The cardioverter/defibrillator includes five terminals 4, 4a, 5, 6 and 7 for connecting to the various electrodes so as to accomplish both sensing and discharging functions as will be described in detail below.

Coupled to the cardioverter/defibrillator 2 is a catheter electrode arrangement. The catheter electrode may be of the type described in U.S. Pat. No. 4,603,705. Specifically, the catheter electrode 8 is a flexible electrode that includes a distal portion 10 formed of a conductive spring electrode defined by the perimeter of the catheter and a proximal portion 12 similarly formed of a conductive spring electrode defined by the catheter. The spring electrodes at the distal and proximal portions 10, 12 are close-wound electrically conductive wires, preferably wound to approximately 20 turns per inch. This provides a continuous electrically conductive surface which maintains its flexibility while still lowering the impedance of the electrodes and thus permittting more current to be delivered for a given discharge. Other electrode configurations may be employed, such as ring-type electrodes.

The catheter electrode 8 is inserted intravenously to a position such that the distal electrode 10 is positioned in the right ventricular apex 14 of the heart and the proximal electrode 12 is positioned in the superior vena cava region 16 of the heart. It should be appreciated that, as the term is used herein, the superior vena cava region 16 includes portions of the right atrium 18. That is, the positioning of the proximal electrode 12 may be partially or wholly within the right atrium 18 rather than entirely within the superior vena cava 16, the dimensions of the patient's heart and the most effective discharge pattern.

The distal electrode 10 is electrically connected, via two conductors 20 and 20a that extend along the length of the catheter 8, to first and second terminals 4 and 4a, respectively, of the cardioverter/defibrillator. The proximal electrode is similarly connected by a conductor 22 to a third terminal 5 of the cardioverter/defibrillator. The distal and proximal electrodes preferably are electrically isolated from each other, yet can be connected together by means of internal switching circuitry in the cardioverter/defibrillator 2, or by means of an external "Y" connector thereby eliminating the need for an additional port in the device header.

As described in the incorporated Patent No. 4,603,705, the electrical surface area of the distal electrode 10 is approximately in the range of 300 to 500 sq. mm. Other surface areas might be chosen. Further, the spacing between the rearwardmost portion of the distal electrode 10 and the forwardmost portion of the proximal electrode 12 is approximately 8 to 14 cm. Such a distance is chosen so that, for the majority of human heart sizes, the distal electrode 10 is within the right ventricular apex and the proximal electrode 12 is in the superior vena cava/right atrium region.

As also described in the patent, a distal sensing and pacing tip electrode 11 may be included on the catheter. The distal tip 11, in conjunction with the distal electrode 10 and conductor 20a, provides sensing of the heart rate as well as pacing functions (although the tip can be fired against any of the other electrodes for "unipolar" pacing). The tip 11 is electrically insulated from the distal electrode 10, and is connected to a fourth terminal 6 of cardioverter/defibrillator 2 through the means of a conductor 21. Moreover, the distal electrode 10 and the proximal electrode 12 may be used as an input to a probability density function (PDF) sensing circuit within the cardioverter/defibrillator 2, whereby a PDF signal, indicative of an arrhythmia condition, may be detected. Thus, the implantable cardioverter/defibrillator 2 senses heart rate via electrodes 10, 11, senses PDF signals via electrodes 10, 12 (or 10 and 12, 24), and issues cardioverting/defibrillating pulses via electrodes 10, 12 and 24 (in a manner to be described) when the sensed heart rate/PDF signals satisfy certain predetermined criteria.

A flexible patch electrode 24 is electrically connected to the cardioverter/defibrillator 2 at its fifth terminal 7, and is subcutaneously positioned outside the thoracic cavity. That is, the patch electrode 24 is positioned between the skin 26 and the rib cage 28. This subcutaneous implantation does not require any opening of the rib cage, or thoracic cavity 28.

The patch electrode preferably is positioned slightly more posterior than just proximate the left ventricular apex 30 of the heart. The precise position for the patch electrode may vary from patient to patient, but is selected so as to attain maximum discharge through both ventricles, depending upon the patient's anatomy and/or pathophysiology.

The patch electrode 24 may be similar to that depicted in U.S. design Pat. No. Des. 273,514. The patch electrode is a flexible, conformal, generally planar electrode having a metallic mesh on the surface facing the heart, and flexible insulating material on its rear side. The patch electrode may have a surface area of 13.5 sq.cm. although other surface areas effectively may be employed depending upon the energy levels required.

In operation, the automatic implantable cardioverter/defibrillator 2, after detecting a life-threatening abnormal heart rhythm, will actuate internal switching circuitry to electrically connect together the two electrodes on the bipolar catheter 8, and then will issue a cardioverting or defibrillating pulse through its pulse generator section. At least one high energy pulse or shock is issued to the implantable electrodes by providing a voltage pulse across the patch electrode 24 and the combination of the distal electrode 10 and the proximal electrode 12 of the catheter 8. The high energy pulse can be an exponentially decaying truncated voltage, as is depicted in the drawing at 34. And preferably, the common catheter electrodes are connected, as illustrated, at cathode potential, while the patch electrode is connected at anode potential. In this manner, a uniform, widely disbursed electrical field is believed to be created across the heart, with the majority of the electrical current passing through both ventricles, that more effectively depolarizes the ailing myocardium using electrical energies lower than otherwise would be effective. If unsuccessful, additional pulses may be issued, which may be at increased energy levels.

As explained above, it is preferable to utilize a bipolar catheter electrode and a subcantaneous patch electrode. However, it is believed that the electrical effectiveness of the present invention also could be accomplished by utilizing one or two patch electrodes applied outside the heart to replace one or both of the electrodes on the bipolar catheter. Similarly, the subcantaneous patch electrode could be placed inside the pericardial sac or directly on the heart. While such alternative electrodes and placements are believed to be electrically equivalent to the preferred embodiment described above, that is, able to deliver a widely disbursed pattern of uniform electrical energy, the surgical implant procedure would, of course, be far more complex. Furthermore, rather than a subcutaneous patch, it may be possible to use a relatively small disc or a large surface area elongated electrode. And, when the term "region of the left ventricle" is used, it is intended to cover electrode placements likely to be near the apex of the left ventricle, where the discharge of electrical current through both ventricles is maximized.

Above, specific embodiments of the present invention have been described. It should be appreciated, however, that this description has been given for purposes of illustration only, and is in no way intended to limit the scope of the present invention. Rather, it is the intention that the present invention be limited only as defined in the appended claims.

What is claimed is:

1. In an automatic implantable cardioverter/defibrillator system for delivering electrical discharges to the heart of a patient to restore normal cardiac rhythm, the system including a pulse generator having terminals of opposite polarity for generating an electrical shock to implantable electrodes, the improvement comprising:

an intravascular catheter insertable within the heart of a patient having a first, distal electrode on the catheter for positioning in the right ventricle, and a second, proximal electrode on the catheter, spaced from the first electrode, for positioning in the superior vena cava region;

a subcutaneous patch electrode for positioning outside the thoracic cavity in the region of the left ventricle, said subcutaneous patch electrode being connected to a terminal of said pulse generator of one polarity;

electrical conducting means for electrically connecting together said first electrode and said second electrode, and connecting such electrodes to a terminal of said pulse generator of an opposite polarity; and discharge means in said pulse generator for supplying electrical energy between said terminals of opposite polarity and hence between said subcutaneous patch electrode and the commonly connected first and second electrodes of said catheter to produce a uniform electric field across the heart with the majority of the electrical current of said electric field passing through both ventricles of the heart.

2. The implantable cardioverter/defibrillator system of claim 1 wherein said pulse generator emits at least one high energy shock to the implantable electrodes to create an electrical field across the heart between the combined first and second electrodes and the subcutaneous patch electrode.

3. The implantable cardioverter/defibrillator system of claim 1 wherein said first and second electrodes are defined by closely-wound electrically conductive wire about the perimeter of the catheter.

4. The implantable cardioverter/defibrillator system of claim 1 wherein said patch electrode comprises a substantially planar, flexible patch, one surface formed of metallic mesh for facing the left ventricle, the opposite surface formed of electrically insulative material.

5. The implantable cardioverter/defibrillator system of claim 1 wherein said catheter further includes a third electrode at the distal tip of said catheter, wherein said first and third electrodes can provide a sensing input to the cardioverter/defibrillator and a pacing pulse output to the heart.

6. A method of automatically cardioverting/defibrillating the heart of a patient comprising the steps of:
    detecting an arrhythmic condition of the heart;
    automatically applying a voltage pulse of a magnitude sufficient to restore normal cardiac rhythm between, firstly, a pair of electrodes, one being located within the right ventricle of the heart and the other being positioned within the superior vena cava region of the heart, and, secondly, a third electrode positioned in the region of the left ventricle outside the thoracic cavity.

7. The method of claim 6 wherein said third electrode is positioned subcutaneously slightly more posterior than just proximate the left ventricular apex.

8. The method of claim 6 wherein said step of automatically applying a voltage pulse comprises applying an exponentially decaying voltage pulse.

9. The method of claim 8 wherein said step of automatically applying a voltage pulse comprises applying a truncated exponentially decaying voltage pulse.

10. An automatic fully implantable pulse generator system for delivering electrical shocks to the heart of a patient to restore normal cardiac rhythm, the system comprising:
    means for sensing the rhythm of the heart and for detecting abnormal rhythms in need of electrical shock to restore normal rhythm;
    first electrode means adapted to be located in the right ventricle;
    second electrode means adapted to be located in the superior vena cava region;
    third electrode means adapted to be located in the region of the left ventricle;
    means for connecting together said first and second electrode means; and
    means for delivering electrical cardioverting shocks between said third electrode means and the commonly connected first and second electrode means when said abnormal rhythms are sensed.

11. The system of claim 10 wherein said first and second electrode means are mounted on an intravascular catheter.

12. The system of claim 11 and further including fourth electrode means mounted on said intravascular catheter; and means for delivering electrical pacing shocks to the heart through said fourth electrode means.

13. The system of claim 10 wherein said first and second electrode means are connected to the cathode of the pulse generator upon delivery of electrical shocks, and said third electrode means is connected to the anode of the pulse generator upon delivery of electrical shocks.

14. The system of claim 10 wherein said third electrode means is in the form of a patch electrode with a conductive surface for facing the heart and an insulative surface for facing away from the heart.

15. A method of automatically cardioverting/defibrillating the heart of a patient comprising the steps of;
   detecting an arrhythmic condition of the heart;
   automatically applying a voltage pulse of a magnitude sufficient to restore normal, cardiac rhythm between, firstly, a first electrode located in the right ventricle of the heart and a second electrode located in the region of the superior vena cava of the heart, and, secondly, a third electrode located in the region of the left ventricle of the heart.

16. The method of claim 15 wherein said first and second electrodes are located on a single intravascular catheter.

17. The method of claim 16 wherein said third electrode is positioned subcutaneously.

18. The method of claim 17 wherein said third electrode is a patch electrode.

* * * * *